Figure 1:
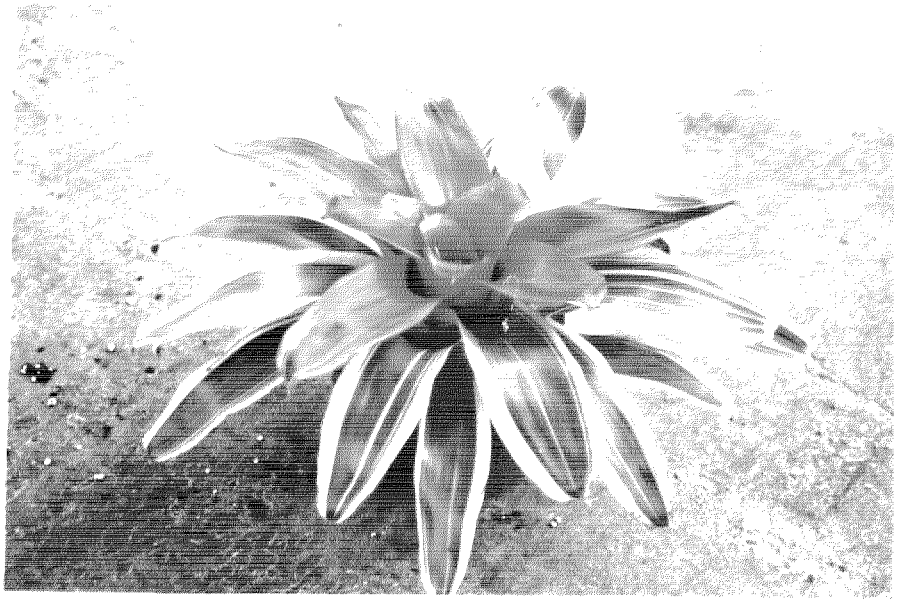

US00PP10816P

United States Patent [19]

Skotak, Jr.

[11] Patent Number: Plant 10,816

[45] Date of Patent: Mar. 2, 1999

[54] NEOREGELIA PLANT NAMED 'FRANCA'

[76] Inventor: Chester Skotak, Jr., Apt 652, Alajuela, Costa Rica

[21] Appl. No.: 893,564

[22] Filed: Jul. 11, 1997

[51] Int. Cl.[6] ..... A01H 5/00

[52] U.S. Cl. ..... Plt./88.8

[58] Field of Search ..... Plt./88.8

[56] References Cited

U.S. PATENT DOCUMENTS

P.P. 9,598 7/1996 Skotak, Jr. ..... Plt./88.8

P.P. 9,599 7/1996 Skotak, Jr. ..... Plt./88.8

*Primary Examiner*—Howard J. Locker

*Assistant Examiner*—Kent L. Bell

*Attorney, Agent, or Firm*—Foley & Lardner

[57] ABSTRACT

A new and distinct cultivar of Neoregelia plant named 'Franca', characterized by its leaves with a creamy white margin (R.H.S. 160B) and dark green center (R.H.S. 131A); the innermost leaves at the center of the rosette, when in flower, are overlayed with pink (R.H.S. 59C); the innermost leaves at the center of the rosette hold their pink color for 3 to 5 months during and after flowering; and the plant produces large numbers of offsets.

2 Drawing Sheets

1

The present invention comprises a new and distinctive cultivar of Neoregelia hybrid, botanically known as Neoregelia and hereinafter referred to by the name 'Franca'.

Neoregelia species are tank epiphytes with stemless inflorescences and flowers that barely rise above the water in the center of the plants. 'Franca' can be advantageously grown as a single pot plant in order to display its symmetrically rosette plant form.

The new cultivar is a product of a planned breeding program, and was originated from a cross made by the inventor Chester Skotak, Jr. during such program in Balsa, Costa Rica in 1988. The female or seed parent was an unnamed plant of *Neoregelia carolinae lineata*×*Neoregelia concentrica*. The male or pollen parent was *Neoregelia carolinae* 'Perfecta'.

'Franca' was discovered and selected as a flowering plant within the progeny of the stated cross by Chester Skotak, Jr. in 1991 in a controlled environment in a nursery in Balsa, Costa Rica.

Subsequent asexual reproduction by removal of offsets has demonstrated that the combination of characteristics as herein disclosed for the new cultivar are firmly fixed and are retained through successive generations of asexual reproduction.

The new cultivar has not been observed under all possible environmental conditions. The phenotype may vary with variations in environment such as temperature, light intensity, and day length, without, however, any variation in the genotype of the plant.

The following traits have been repeatedly observed and are determined to be basic characteristics of 'Franca' which in combination distinguish this Neoregelia as a new and distinct cultivar:

1. Leaves have a creamy white margin (R.H.S. 160B) and dark green center (R.H.S. 131A).

2. The innermost leaves at the center of the rosette, when in flower, are overlayed with pink (R.H.S. 59C).

3. The innermost leaves at the center of the rosette hold their pink color for 3 to 5 months during and after flowering.

4. The plant produces large numbers of offsets.

The new variety Neoregelia 'Franca' can be compared to plants of the species *Neoregelia carolinae*. 'Franca' has a well-developed rosette of leaves and is more compact than *Neoregelia carolinae*. The center color of the leaves when in flower flushes to a nice pink (R.H.S. 59C).

In the photographic drawings, FIG. 1 comprises a side perspective view of a typical plant of the new cultivar.

2

Figure 2:
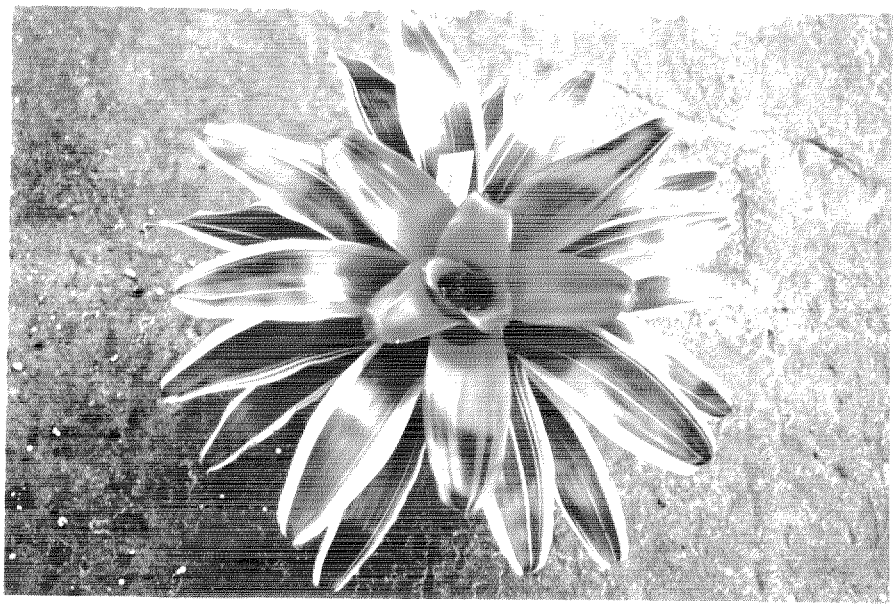

The photo comprising FIG. 2 is a top view of the plant.

The following observations, measurements and values describe plants grown in Balsa, Costa Rica and Apopka, Fla., under greenhouse conditions which closely approximate those generally used in horticultural practice. Color references are made to The Royal Horticultural Society (R.H.S.) Colour Chart, except where general color terms of ordinary significance are used.

Classification:

*Botanical.*—Neoregelia hybrid, cv. 'Franca'.

*Commercial.*—Neoregelia 'Franca'.

Parentage:

*Male parent.*—*Neoregelia carolinae* 'Perfecta'.

*Female parent.*—*An unnamed plant of Neoregelia carolinae lineata*×*Neoregelia concentrica.*

Plant description: Vegetative by removal of offsets.

*Form.*—*From* 20 to 22 cm tall when grown in 12.5 cm pots and approximately 45 cm or more in overall diameter when fully grown.

*Growth habit.*—Spreading rosette.

Leaves:

*Shape.*—Blades lingulate, recurved, broadly rounded and apiculate.

*Size.*—Length about 20–29 cm; width is 2.5 cm at tip and approximately 5 cm at middle.

*Margin.*—Fine toothed.

*Surface texture.*—Smooth.

*Veins or ribs.*—None.

*Color (R.H.S.).*—Upper surface: Creamy white (160B) and dark green center (131A), with slight variegation at the edges. The innermost leaves are overlayed with pink (59C) and hold their color for approximately 3 to 5 months at the time of flowering. Lower surface: Generally similar.

*Number of leaves.*—Average 30.

Rosette:

*Leaves forming the socket.*—short and about 5 cm wide. The socket is about 3 cm in overall diameter.

*Color.*—Pink to purple (59C). The leaves at the edge of the socket have more leaf margins and tips are dark green.

*Flowers.*—Arrangement: Deeply sunken rosette, simple and many flowered. Color: Petal apex violet-blue 91A with white base. Fruit: White, ovary ellipsoid and approximately 13 mm long. Duration of the flowers: Individual flowers last one day but flowering is continuous for 3 to 4 weeks.

Reproductive organs:

*Stamen.*—Pale yellow.

*Pistils.*—White; ovary is ellipsoid and approximately 13 mm long and 5 mm in diameter.

Disease resistance: Good resistance to fungi and insects exhibited in Costa Rica.

General observations: 'Franca' produces large numbers of offsets. Individual plants may produce up to 20 offsets per mature plant.

I claim:

1. A new and distinct Neoregelia plant named 'Franca', as illustrated and described within a 3 to 10 month period.

* * * * *